(12) United States Patent
Takaori et al.

(10) Patent No.: US 9,457,028 B2
(45) Date of Patent: Oct. 4, 2016

(54) PHARMACEUTICAL COMPOSITION FOR USE IN PREVENTION OR TREATMENT OF CANCER

(71) Applicant: KYOTO UNIVERSITY, Kyoto (JP)

(72) Inventors: Akifumi Takaori, Kyoto (JP); Shunichi Takeda, Kyoto (JP); Masayuki Kobayashi, Kyoto (JP); Kohei Tada, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/770,289

(22) PCT Filed: Feb. 27, 2014

(86) PCT No.: PCT/JP2014/054893
§ 371 (c)(1),
(2) Date: Aug. 25, 2015

(87) PCT Pub. No.: WO2014/133085
PCT Pub. Date: Sep. 4, 2014

(65) Prior Publication Data
US 2016/0000796 A1 Jan. 7, 2016

(30) Foreign Application Priority Data
Feb. 27, 2013 (JP) ................................ 2013-037426

(51) Int. Cl.
*A01N 43/90* (2006.01)
*A61K 31/52* (2006.01)
*A61K 45/06* (2006.01)

(52) U.S. Cl.
CPC ............... *A61K 31/52* (2013.01); *A61K 45/06* (2013.01)

(58) Field of Classification Search
CPC ..................................................... A61K 31/52
USPC ...................................................... 514/263.4
See application file for complete search history.

(56) References Cited

U.S. PATENT DOCUMENTS

2009/0149397 A1   6/2009   Ossovskaya et al.

FOREIGN PATENT DOCUMENTS

| WO | 98/52570 | 11/1998 |
|---|---|---|
| WO | 2009/073869 | 6/2009 |

OTHER PUBLICATIONS

Rossi A et al, Int J Cancer., 2009, 125(1), 235-43.*
Toshinori et al., Japanese Journal of Clinical Medicine, 2004, 62(7),1271 to 1276.*
Hill SA et al, J Infect Dis., 2003, 188(3), 424-7.*
Makinson A, et al, J Thorac Oncol., 2010, 5(4), 562-71.*
Kato T et al., Jpn J Clin Oncol., 2005, 35(6), 349-52.*
Carlini et al. One (2010), 5(12), e14221.*
Olivero, "Mechanisms of Genotoxicity of Nucleoside Reverse Transcriptase Inhibitors", Environmental and Molecular Mutagenesis, 2007, vol. 48, pp. 215-223.
Gill et al., "Treatment of Adult T-Cell Leukemia-Lymphoma with a Combination or Interferon ALFA and Zidovudine", The New England Journal of Medicine, 1995, vol. 332, pp. 1744-1748.
Bazarbachi et al., "Meta-Analysis on the Use of Zidovudine and Interferon-Alfa in Adult T-Cell Leukemia/Lymphoma Showing Improved Survival in the Leukemic Subtypes", Journal of Clinical Oncology, 2010, vol. 28, No. 27, pp. 4177-4183.
Bazarbachi et al., "Evidence Against a Direct Cytotoxic Effect of Alpha Interferon and Zidovudine in HTLV-1 Associated Adult T Cell Leukemia/Lymphoma", Leukemia, 2000, vol. 14, pp. 716-721.
Hill et al., "Susceptibility of Human T Cell Leukemia Virus Type I to Nucleoside Reverse Transcriptase Inhibitors", The Journal of Infectious Diseases, 2003, vol. 188, pp. 424-427.
Rossi et al., "The Antiretroviral Nucleoside Analogue Abacavir Reduces Cell Growth and Promotes Differentiation of Human Medulloblastoma Cells", International Journal of Cancer, 2009, vol. 125, pp. 235-243.
Ide et al., "Telomere and Telomerase as Targets for Anti-Cancer Drugs", Japanese Journal of Clinical Medicine, 2004, vol. 62, pp. 1271-1276.
Makinson et al., "Interactions Between Cytotoxic Chemotherapy and Antiretroviral Treatment in Human Immunodeficiency Virus-Infected Patients with Lung Cancer", Journal of Thoracic Oncology, 2010, vol. 5, pp. 562-571.
Kato et al., "A Long-term Survival Case of Small Cell Lung Cancer in an HIV-Infected Patient", Japanese Journal of Clinical Oncology, 2005, vol. 35, pp. 349-352.
Vanmassenhove et al., "Fanconi Syndrome in Lymphoma Patients: Report of the First Case Series", Nephrology Dialysis Transplantation, 2010, vol. 25, pp. 2516-2520.
International Preliminary Report on Patentability issued Aug. 27, 2015 in corresponding International Application No. PCT/JP2014/054893.
International Search Report issued Jun. 3, 2014 in corresponding International Application No. PCT/JP2014/054893.
Extended European Search Report issued Jul. 1, 2016, in corresponding European Application No. 14756518.8.
Shay et al., "A Survey of Telomerase Activity in Human Cancer", European Journal of Cancer, vol. 33, No. 5, 1997, pp. 787-791.
Tada et al., "Abacavir, an Anti-HIV-1 Drug, Targets TDP1-Deficient Adult T Cell Leukemia", Science Advances, vol. 1, No. 3, 2015, pp. 1-13.

* cited by examiner

*Primary Examiner* — Nizal Chandrakumar
(74) *Attorney, Agent, or Firm* — Wenderoth, Lind & Ponack, L.L.P.

(57) ABSTRACT

Abacavir, a nucleoside analog reverse transcriptase inhibitor, has been found to exhibit an anti-cancer activity on ATL cells in vitro without inhibiting DNA replication of normal cells. Abacavir or a pharmaceutically acceptable derivative thereof is useful as an active ingredient of a pharmaceutical composition for use in the prevention or the treatment of cancer, in particular a cancer whose DNA repair system is impaired such as breast cancer or adult T-cell leukemia.

8 Claims, 14 Drawing Sheets

(A) Cell proliferation (B) HTLV-1 p19 ELISA (A)

(B)

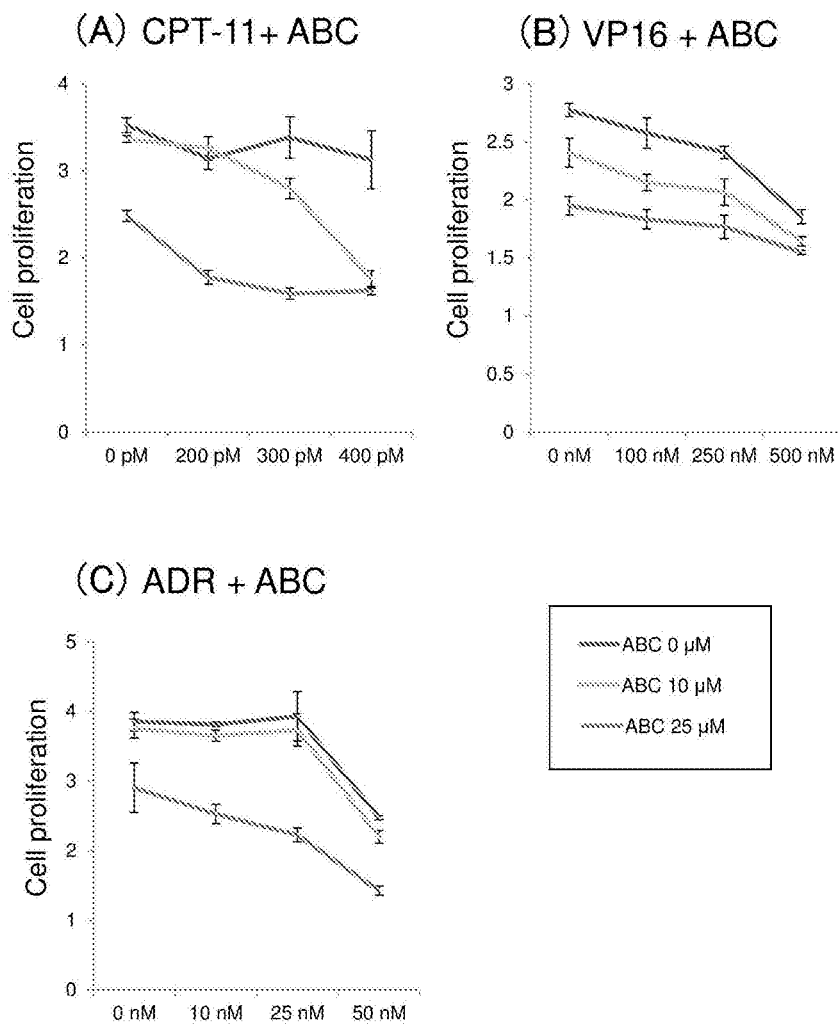

PHARMACEUTICAL COMPOSITION FOR USE IN PREVENTION OR TREATMENT OF CANCER

TECHNICAL FIELD

The present invention relates to a pharmaceutical composition for use in the prevention or the treatment of cancer. Particularly, the present invention relates to a pharmaceutical composition for use in the prevention or the treatment of cancer comprising abacavir or a pharmaceutically acceptable derivative thereof as an active ingredient.

BACKGROUND ART

Nucleoside analogue reverse transcriptase inhibitors (NRTIs) have been developed as drugs against human immunodeficiency virus type 1 (hereinafter referred to as "HIV-1") and currently used as major therapeutic HIV drugs. Nevertheless, a prototype thereof, i.e., zidovudine (AZT), is known to inhibit not only reverse transcription of viruses but also DNA replication of normal cells (see, Non Patent Literature 1). Various types of Nucleoside analogue reverse transcriptase inhibitors are also known to have an antiviral effect against human T-cell leukemia virus type 1 (hereinafter referred to as "HTLV-1"), which is a human retrovirus similar to HIV-1. Further, combination therapy with interferon (IFN) and zidovudine has been known as effective for adult T-cell leukemia (hereinafter referred to as "ATL") caused by HTLV-1 infection (see Non Patent Literatures 2 and 3). However, zidovudine is reported to have no anti-cancer effect against ATL cells in vitro (see Non Patent Literature 4) and thus mechanism of action of zidovudine on ATL cells remains poorly understood.

One of NRTIs, abacavir (ABC), is clinically used as an anti-HIV drug and also reported to have an anti-HTLV-1 effect (see Non Patent Literature 5). However, abacavir is not known to have an anti-cancer effect.

CITATION LIST

Non Patent Literatures

Non Patent Literature 1: Environ Mol Mutagenesis 48: 215, 2007
Non Patent Literature 2: NEJM 332: 1744, 1.995
Non Patent Literature 3: J Clin Oncol 28: 4177, 2010
Non Patent Literature 4: Leukemia 14: 716, 2000
Non Patent Literature 5: J Infect Dis 188: 424, 2003

SUMMARY OF INVENTION

An object of the present invention is to provide a novel pharmaceutical composition for use in the prevention or the treatment of cancer which comprises a nucleoside analogue reverse transcriptase inhibitor as an active ingredient and has reduced side effects on normal cells by finding a nucleoside analogue reverse transcriptase inhibitor exhibiting an anti-cancer activity on ATL cells in vitro without inhibiting DNA replication of normal cells.

To achieve the above object, the present invention includes the following embodiments.

[1] A pharmaceutical composition for use in the prevention or the treatment of cancer, comprising abacavir or a pharmaceutically acceptable derivative thereof as an active ingredient.

[2] The pharmaceutical composition for use according to [1], which is for use in the prevention or the treatment of a cancer whose DNA repair system is impaired.

[3] The pharmaceutical composition for use according to [2], in which the cancer whose DNA repair system is impaired is a cancer expressing a reduced level of TDP1.

[4] The pharmaceutical composition for use according to any one of [1] to [3], which is for use in the prevention or the treatment of lung cancer or cancer caused by infection with human T-cell leukemia virus type 1.

[5] The pharmaceutical composition for use according to any one of [1] to [4], which is for use in the prevention or the treatment of adult T-cell leukemia.

[6] The pharmaceutical composition for use according to any one of [1] to [5], which is used in combination with a PARP inhibitor.

[7] The pharmaceutical composition for use according to any one of [1] to [5], which is used in combination with a topoisomerase inhibitor.

[8] The pharmaceutical composition for use according to any one of [1] to [7], which has a DNA cleavage activity.

[9] The pharmaceutical composition for use according to any one of [1] to [7], which has a cell cycle arrest-inducing activity and/or an apoptosis-inducing activity.

[10] A pharmaceutical composition for use in the prevention or the treatment of a disease caused by HTLV-1 infection, comprising abacavir or a pharmaceutically acceptable derivative thereof as an active ingredient.

The present invention provides a pharmaceutical composition for use in the prevention or the treatment of cancer that exhibits an anti-cancer activity without inhibiting DNA replication of normal cells. That is, a novel pharmaceutical composition for use in the prevention or the treatment of cancer having reduced side effects on normal cells is provided.

BRIEF DESCRIPTION OF DRAWINGS

FIG. 20 shows the effect of combination of abacavir and a topoisomerase inhibitor on an HTLV-1-infected cell line, MT2. The graphs (A), (B), and (C) show the results of combination with CPT-11, VP16, and ADR, respectively.

DESCRIPTION OF EMBODIMENTS

Figure 1:
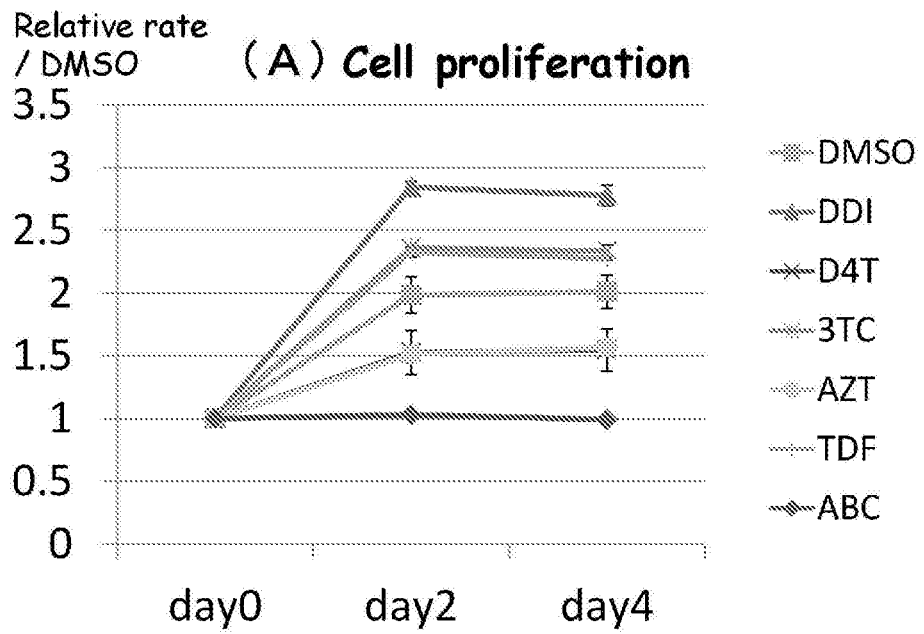
FIG. 1 shows the effects of six types of nucleoside analogue reverse transcriptase inhibitors on cellular proliferation and viral production of HTLV-1-producing cell line, MT2. The graph (A) shows the results cellular proliferation and the graph (B) shows the results of viral production.
Figure 1:
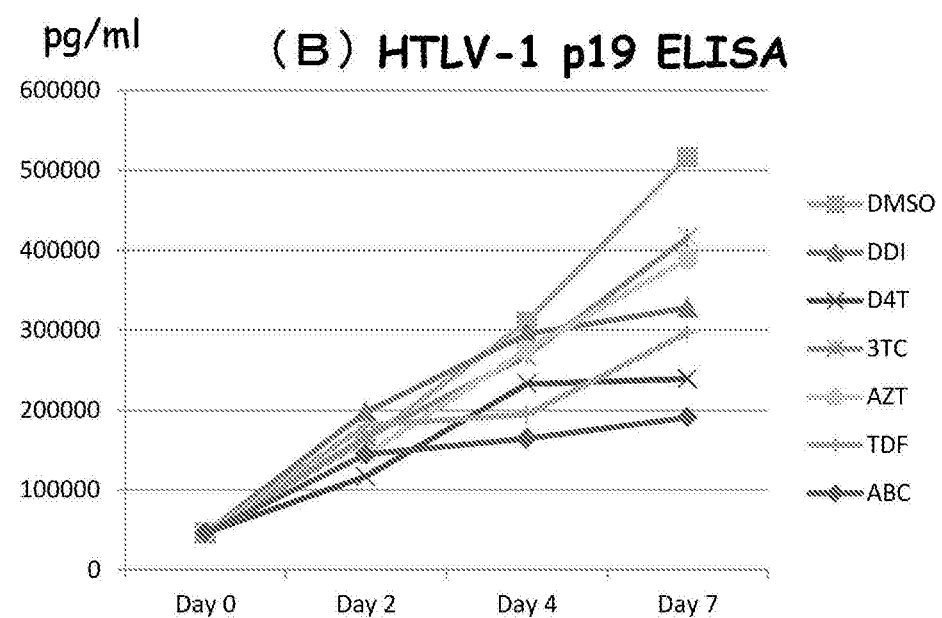

The present inventors have found that abacavir, among various types of nucleoside analogue reverse transcriptase inhibitors, exhibits the most potential suppressive effect on cellular proliferation of HTLV-1-infected cells and ATL cells, while does not exhibit the effect on non-HTLV-1-infected cells. The present inventors have also found that abacavir affects DNA repair system to induce DNA double-strand break; exhibits a synergetic effect with a PARP inhibitor; and induces cell-cycle arrest and apoptosis. The present inventors have further found that abacavir exhibits a suppressive effect on cellular proliferation of non-HTLV-1-infected cancer cells when the DNA repair system of the cells is impaired. The present inventors have still further found that abacavir exhibits a suppressive effect on cellular proliferation of cancer cells expressing a reduced level of TDP1, which is a DNA repair enzyme; and that abacavir exhibits a synergetic effect with a topoisomerase inhibitor.

Abacavir is a compound having the following chemical structure and its chemical name is (−)-(1S,4R)-4-[2-amino-6-(cyclopropylamino)-9H-purin-9-yl]-2-cyclopentene-1-methanol).

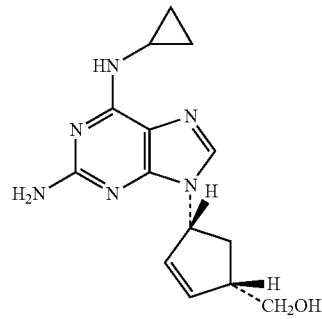

As used herein, "a pharmaceutically acceptable derivative" refers to any one of pharmaceutically acceptable salts, solvates, esters or salts of the esters, and any other compounds that provides, directly or indirectly, a desired active ingredient or an active metabolite or residue thereof when it is administered to a living body such as a mammal.

Examples of pharmaceutically acceptable salts of abacavir include salts of alkali metals (e.g., potassium, sodium, and lithium), salts of alkaline earth metals (e.g., calcium and magnesium), ammonium salts (e.g., tetramethyl ammonium salt and tetrabutyl ammonium salt), salts of organic amines (e.g., triethylamine, methylamine, dimethylamine, cyclopentyl amine, benzylamine, phenethylamine, piperidine, monoethanolamine, diethanolamine, tris(hydroxymethyl)methylamine, lysine, arginine, and N-methyl-D-glucamine) and acid addition salts (e.g., inorganic acid salts such as a hydrochloride, a hydrobromide, a hydroiodide, a sulfate, a phosphate and a nitrate; and organic acid salts such as an acetate, a trifluoroacetate, a lactate, a tartrate, an oxalate, a fumarate, a maleate, a benzoate, a citrate, a methanesulfonate, an ethanesulfonate, a benzene sulfonate, a toluene sulfonate, an isethionate, a glucoronate, and a gluconate). Preferably, the salt is a succinate and hemi-sulfate.

Abacavir may be produced by the method described in European patent No. 0434450 or WO95/21161. Abacavir succinate may be prepared by the method described in WO96/06844. Abacavir hemi-sulfate may be prepared by the method described in WO98/52949.

Cancers to be prevented or, treated by the pharmaceutical composition of the present invention is not limited to particular cancers. Preferably, the pharmaceutical composition of the present invention is used for a cancer whose DNA repair system is impaired. Examples of the cancer whose DNA repair system is impaired include breast cancer, ovarian cancer, skin cancer, colon cancer, lung cancer and lymphocytic leukemia. Further, a cancer caused by HTLV-1 infection is included in the cancer whose DNA repair system is impaired. Accordingly, a cancer caused by HTLV-1 infection is suitably prevented or treated with the pharmaceutical composition of the present invention. The cancer caused by HTLV-1 infection includes ATL. The present inventors have confirmed that cells of a cancer caused by HTLV-1 infection express a reduced level of a DNA repair enzyme, TDP1. Thus, it is preferable that the pharmaceutical composition of the present invention is used for a cancer expressing a reduced level of TDP1. Examples of the cancer expressing a reduced level of TDP1 include ATL and lung cancer. TDP1

(Tyrosyl-DNA phosphodiesterase 1) is a DNA repair protein and known to be involved, in particular, in repairing single-stranded DNA break. Reduced expression of TDP1 in a cancer may be determined by measuring the amount of TDP1 protein or TDP1 mRNA in cancer cells by a known method such as Western blot or quantitative RT-PCR and comparing the amount with that of cells whose DNA repair system is unimpaired.

Abacavir exhibits a strong suppressive effect on cellular proliferation and viral production of an HTLV-1-infected non-cancerous cell MT2. Thus, the pharmaceutical composition of the present invention is particularly useful as a drug for preventing development of ATL in a HTLV-1 carrier.

Also, since abacavir exhibits a strong suppressive effect on cellular proliferation and viral production of HTLV-1-infected non-cancerous cell MT2, the pharmaceutical composition of the present invention is useful for the prevention and/or the treatment of any disease caused by HTLV-1 infection. Examples of the disease caused by HTLV-1 infection include, in addition to ATL, inflammatory diseases such as HAM/TSP (HTLV-I associated myelopathy/tropical spastic paraparesis), HTLV-1 associated uveitis, and HTLV-1 associated arthropathy. Thus, the disclosure also provides a pharmaceutical composition for use in the prevention or the treatment of a disease caused by HTLV-1 infection comprising abacavir or a pharmaceutically acceptable derivative thereof as an active ingredient.

Abacavir has an activity for inducing DNA cleavage, particularly DNA double-strand break. Thus, the pharmaceutical composition of the present invention is useful as an inducer of DNA cleavage or DNA double-strand break. In addition, abacavir has an activity of inducing cell cycle arrest and apoptosis. Thus, the pharmaceutical composition of the present invention is also useful as an inducer of cell cycle arrest or apoptosis.

The pharmaceutical composition of the present invention may be formulated by combining abacavir or a pharmaceutically acceptable derivative thereof as an active ingredient with a pharmaceutically acceptable carrier and optionally an additive as needed. Specifically, the pharmaceutical composition of the present invention may be oral preparations such as a tablet, a coated tablet, a pill, a powder, a granule, a capsule, a liquid, a suspension and an emulsion; and parenteral preparations such as an injection, an infusion, a suppository, an ointment and a patch. The content of the carrier or additive may be appropriately defined based on the range usually employed in the pharmaceutical field. Examples of the carrier or additive that may be used include, but not particularly limited to, various carriers such as water, saline, other aqueous solvents, aqueous or oily bases, and various additives such as an excipient, a binder, a pH regulator, a disintegrating agent, an absorption accelerator, lubricant, a coloring agent, a flavor and a spice.

Examples of the additive that may be blended to tablets and capsules include a binder such as gelatin, cornstarch, tragacanth or Arabian gum; an excipient such as crystalline cellulose; a swelling agent such as cornstarch, gelatin or alginic acid, a lubricant such as magnesium stearate; a sweetening agent such as sucrose, lactose or saccharin; and a flavoring agent such as peppermint, Akamono oil or cherry. When a formulation is in a form of a capsule, the formulation may further contain a liquid carrier such as an oil in addition to the above materials. An aseptic composition for injection may be prepared in accordance with conventional methods for formulation (for example, by dissolving or suspending an active ingredient in a solvent such as an injection water and natural vegetable oil). Examples of aqueous solutions for injection include saline and isotonic solutions containing glucose and other adjunctive agents such as D-sorbitol, D-mannitol, and sodium chloride, and may be used in combination with an appropriate solubilizing agent, such as an alcohol (e.g., ethanol), a polyalcohol (e.g., propylene glycol and polyethylene glycol) and a nonionic surfactant (e.g., polysorbate 80™ and HCO-50). Examples of oily liquids include sesame oil and soybean oil, and may be used in combination with a solubilizing agent such as benzyl benzoate and benzyl alcohol. Further, a buffer such as phosphate buffer and sodium acetate buffer, a soothing agent such as benzalkonium chloride and procaine hydrochloride, a stabilizer such as human serum albumin and polyethylene glycol, a preservative such as benzyl alcohol and phenol, and an antioxidant may be used in combination.

Abacavir is widely used as an anti-virus chemotherapy agent in clinical sites and thus the pharmaceutical composition of the present invention is safe to use in humans and other mammals including rats, mice, rabbits, sheep, pigs, cows, cats, dogs, and monkeys.

The dosage of abacavir varies depending upon factors such as conditions of persons to be administered, types of targeted cancers, symptoms, and methods of administration, and thus the dosage is finally left to determination by the doctor. For oral administration, the dosage falls within a range of about 0.1 to 120 mg, preferably about 3 to 90 mg, more preferably about 5 to 60 mg per kg of body weight of the person to be administered per day. The total dosage per day may be equal to a single dose or the sum of divided doses.

The anti-cancer activity of the pharmaceutical composition of the present invention is synergistically enhanced in combination with a DNA repair enzyme inhibitor. Examples of the DNA repair enzyme inhibitor include, but not limited to, a PARP (poly(ADP-ribose)polymerase) inhibitor, a TDP1 repair enzyme inhibitor, an inhibitor against a proofreading nuclease activity of a replicative DNA polymerase, an inhibitor against translesion DNA polymerase and an ATR kinase inhibitor. The DNA repair enzyme inhibitor is preferably a PARP inhibitor.

The pharmaceutical composition of the present invention may be used in combination with a different therapeutic agent for cancer. The different therapeutic agent for cancer used in combination is preferably, but not limited to, a chemotherapeutic agent, an immunotherapeutic agent or a hormone therapy agent. Further, the agent of the present invention for use in the prevention or the treatment of cancer may be used in combination with a radiation therapy.

Examples of the chemotherapeutic agent include, but not particularly limited to, alkylating agents such as nitrogen mustard, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylene melamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, ribomustin, temozolomide, treosulfan, trofosfamide, zinostatin stimalamer, adozelesin, cystemustine and bizelesin; metabolic antagonists such as mercaptopurine, 6-mercaptopurine riboside, thioinosine, methotrexate, pemetrexed, enocitabine, cytarabine, cytarabine ocfosphate, ancitabine hydrochloride, 5-FU drugs (e.g., fluorouracil, Tegafur, UFT, doxifluridine, carmofur, galocitabine, emitefur, and capecitabine), aminopterin, nelzarabine, leucovorin calcium, tabloid, butocine, calcium folinate, calcium lebofolinate, cladribine, emitefur, fludarabine, gemcitabine, hydroxycarbamide, pentostatin, piritrexim, indoxuridine, mitoguazone, thiazophrine, ambamustine and bendamustine; anticancer antibiotics such as actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithracin, sarcomycin, carzinophilin, mitotane, zorubicin hydrochloride, mitoxantrone hydrochloride and idarubicin hydrochloride; and plant-derived anticancer agents such as etoposide, etoposide phosphate, vinblastine sulfate, vincristine sulfate, vindesine sulfate, teniposide, paclitaxel, docetaxel, vinorelbine, irinotecan and irinotecan hydrochloride.

Examples of the immunotherapeutic agent include, but not particularly limited to, picibanil, krestin, sizofiran, lentinan, ubenimex, interferon, interleukin, macrophage colony stimulating factor, granulocyte colony-stimulating factor, erythropoietin, lymphotoxin, BCG vaccine, *Corynebacterium parvum*, levamisole, polysaccharide K, procodazole and an anti-CTLA4 antibody.

Examples of the hormonal therapeutic agent include, but not particularly limited to, fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, an anti-estrogen agent (e.g., tamoxifen citrate and toremifene citrate), contraceptive pills, mepitiostane, testololactone, aminoglutethimide, an LH-RH agonist (e.g., goserelin acetate, buserelin, and leuprorelin), droloxifene, epitiostanol, ethinylestradiol, sulfonate, an aromatase inhibitor (e.g., fadrozole hydrochloride, anastrozole, letrozole, exemestane, vorozole, and formestane), an anti-androgen agent (e.g., flutamide, bicalutamide, and nilutamide), a 5α-reductase inhibitor (e.g., finasteride and epristeride), an adrenal cortical hormone drug (e.g., dexamethasone, prednisolone, betamethasone, and triamcinolone) and an androgenic synthetic inhibitor (e.g., abiraterone).

The pharmaceutical composition of the present invention is preferably used in combination with a topoisomerase inhibitor. The anti-cancer activity of the pharmaceutical composition of the present invention is synergistically enhanced in combination with a topoisomerase inhibitor. The topoisomerase inhibitor inhibits the activity of topoisomerase and enters a cleavage site of DNA to inhibit reunion thereof, with the result that DNA remains cleaved and the cancer cell dies. The topoisomerase inhibitor suitable for use in combination with the pharmaceutical composition of the present invention is not limited to particular drugs. Any drug having the above mechanism of action may be suitably used in combination with the pharmaceutical composition of the present invention. Specific examples of the topoisomerase inhibitor include irinotecan hydrochloride (CPT-11), etoposide (VP16), doxorubicin hydrochloride (ADR), nogitecan, daunorubicin hydrochloride, aclarubicin hydrochloride, pirarubicin hydrochloride, epirubicin hydrochloride, zorubicin hydrochloride, mitoxantrone hydrochloride, idarubicin hydrochloride, irinotecan and etoposide phosphate.

In combination with a different therapeutic agent for cancer or a radiation therapy, the agent for use in the prevention or the treatment of cancer of the present invention provides various effects; for example, (1) provides synergetic effects, (2) enables reduced dosage, (3) enables prolonged duration of therapy, and (4) enables sustained therapeutic effects.

The agent for use in the prevention or the treatment of cancer of the present invention and a different therapeutic agent for cancer used in combination may be administered to a subject simultaneously or at different times. The dosage of the combined agent may be defined in accordance with the dosage clinically used and appropriately selected depending upon factors such as subjects, age and weight of subjects, symptoms, duration of administration, types of formulation, methods of administration, and combination thereof.

The present invention also provides the following embodiments:

A method for the prevention or the treatment of cancer, comprising administering an effective amount of abacavir or a pharmaceutically acceptable derivative thereof to a mammal;

Abacavir or a pharmaceutically acceptable derivative thereof for use in the prevention or the treatment of cancer;

Use of abacavir or a pharmaceutically acceptable derivative thereof for the manufacture of a medicament for use in the prevention or the treatment of cancer;

A method for the prevention or the treatment of a disease caused by HTLV-1 infection, comprising administering an effective amount of abacavir or a pharmaceutically acceptable derivative thereof to a mammal;

Abacavir or a pharmaceutically acceptable derivative thereof for use in the prevention or the treatment of a disease caused by HTLV-1 infection; and Use of abacavir or a pharmaceutically acceptable derivative thereof for the manufacture of a medicament for use in the prevention or the treatment of a disease caused by HTLV-1 infection.

EXAMPLES

The present invention will be described more specifically by way of Examples; however, the present invention is not limited to those examples. Unless otherwise specified, the experimental methods were those described in standard protocols in the technical field to which the invention pertains, such as J. Sambrook, E. F. Fritsch & T. Maniatis (Ed.), "Molecular Cloning, A Laboratory Manual (3rd edition)", Cold Spring Harbor Press, Cold Spring Harbor, N.Y. (2001) and F. M. Ausubel, R. Brent, R. E. Kingston, D. D. Moore, J. G. Seidman, J. A. Smith, K. Struhl (Ed.), "Current Protocols in Molecular Biology", John Wiley & Sons Ltd. etc., or modified methods of the same.

Example 1

Effects on Cellular Proliferation and Viral Production of HTLV-1-Producing Cell Line (1) Experimental Materials HTLV-1-producing cell lines, MT2 (transformant with HTLV-1, JCRB cell No: JCRB1210) and HUT102 (ATL-derived cell line, ATCC No: TIB-162), were used.

Six types of nucleoside analogue reverse transcriptase inhibitors: abacavir (ABC), zidovudine (AZT), didanosine (DDI), stavudine (D4T), lamivudine (3TC) and tenofovir (TDF) were used. Each nucleoside analogue reverse transcriptase inhibitor was dissolved in DMSO and added to the medium. Those nucleoside analogue reverse transcriptase inhibitors were obtained from the U.S. NIH AIDS reagent program.

(2) Cellular Proliferation Test

Each nucleoside analogue reverse transcriptase inhibitor was added to the medium for cells at a final concentration of 100 μM. Cells were seeded on a 96-well plate at a concentration of $1 \times 10^4$ cells/100 μL/well and cultured for 4 hours (Day 0), 48 hours (Day 2) or 96 hours (Day 4). A medium added DMSO (solvent control) alone was used as a control. Cellular proliferation was examined by MTS assay. Specifically, after the cells were cultured for a predetermined time, a reagent for cellular proliferation test, Aqueous One Solution Cell Proliferation (trade name, manufactured by Promega), was added to the cells. Four hours later, absorbance at 490 nm was measured. The cellular proliferation was represented by a ratio relative to that of the control (solvent control) on Day 0 that was regarded as 1.

(3) Measurement of Amount of Virus

Each nucleoside analogue reverse transcriptase inhibitor was added to the medium for cells at a final concentration of 100 μM. Cells were seeded on a 96-well plate at a concentration of $1 \times 10^4$ cells/100 μL/well and cultured for 0 hour (Day 0), 48 hours (2 days), 96 hours (4 days) or 168 hours (7 days). At each time point, the medium was collected. The amount of virus contained in the medium collected at each time point (pg/mL) was measured by HTLV-1 P19 ELISA kit (manufactured by Zeptometrix).

(4) Results

Figure 2:
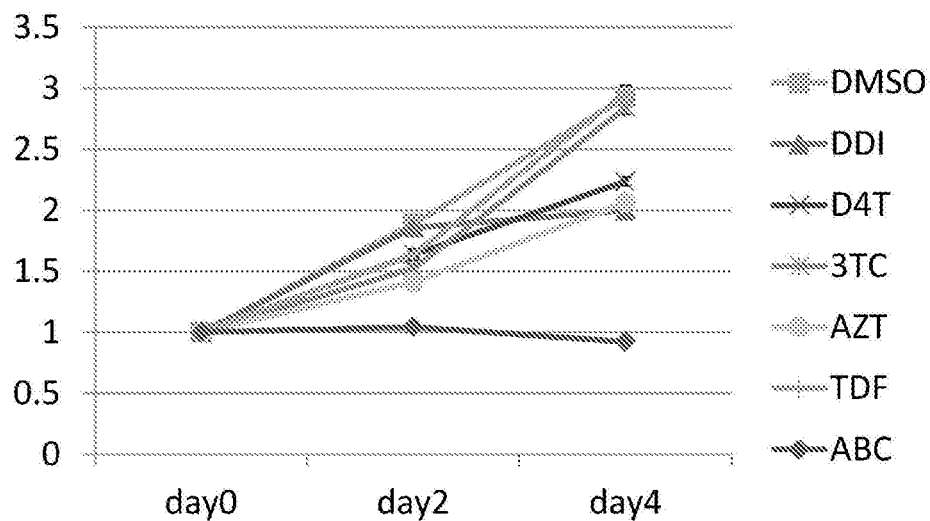
FIG. 2 shows the effects of six types of nucleoside analogue reverse transcriptase inhibitors on cellular proliferation and viral production of HTLV-1-producing cell line, HUT102 (derived from ATL). The graph (A) shows the results of cellular proliferation and the graph (B) shows the results of viral production.
Figure 2:
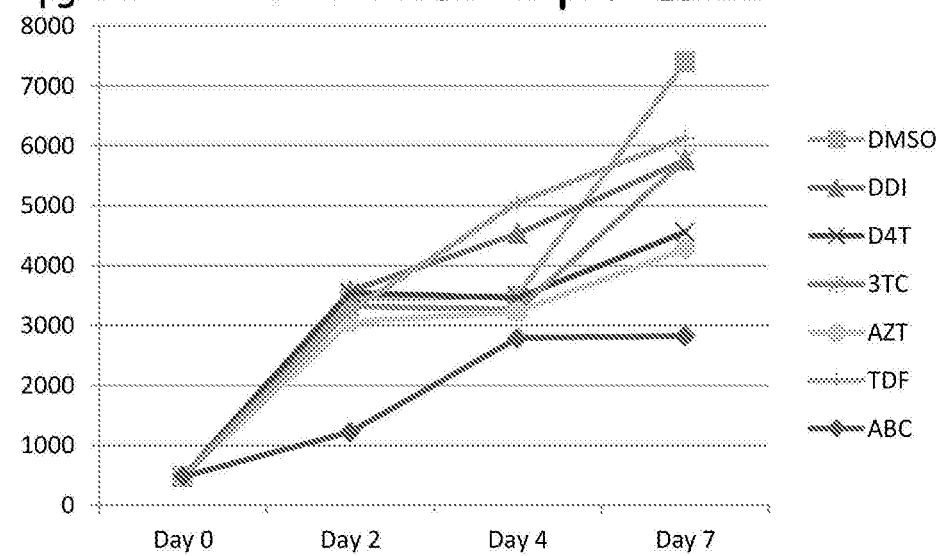

FIGS. 1 and 2 show the results of MT2 and HUT102, respectively. In both FIGS. 1 and 2, the graph (A) shows the results of cellular proliferation and the graph (B) shows the results of viral production. As is apparent from FIGS. 1 and 2, abacavir (ABC in the graphs), among the six types of nucleoside analogue reverse transcriptase inhibitors used in the experiments, most strongly suppressed cellular proliferation and viral production in both cell lines.

Example 2

Effect on Cellular Proliferation of HTLV-1-Infected Cell Line (Non-Virus-Producing ATL Cell Line)

This example used HTLV-1-infected cell lines (non-virus-producing ATL cell lines): ED40515 (−), ED40515 (+), and ATL43T (all were provided by Prof. Michiyuki Maeda who produced the cells); and SYK-11L (+) (prepared in the laboratory of the inventors).

The six types of nucleoside analogue reverse transcriptase inhibitors as used in Example 1 were used and cellular proliferation was examined in the same manner as in Example 1.

Figure 3:
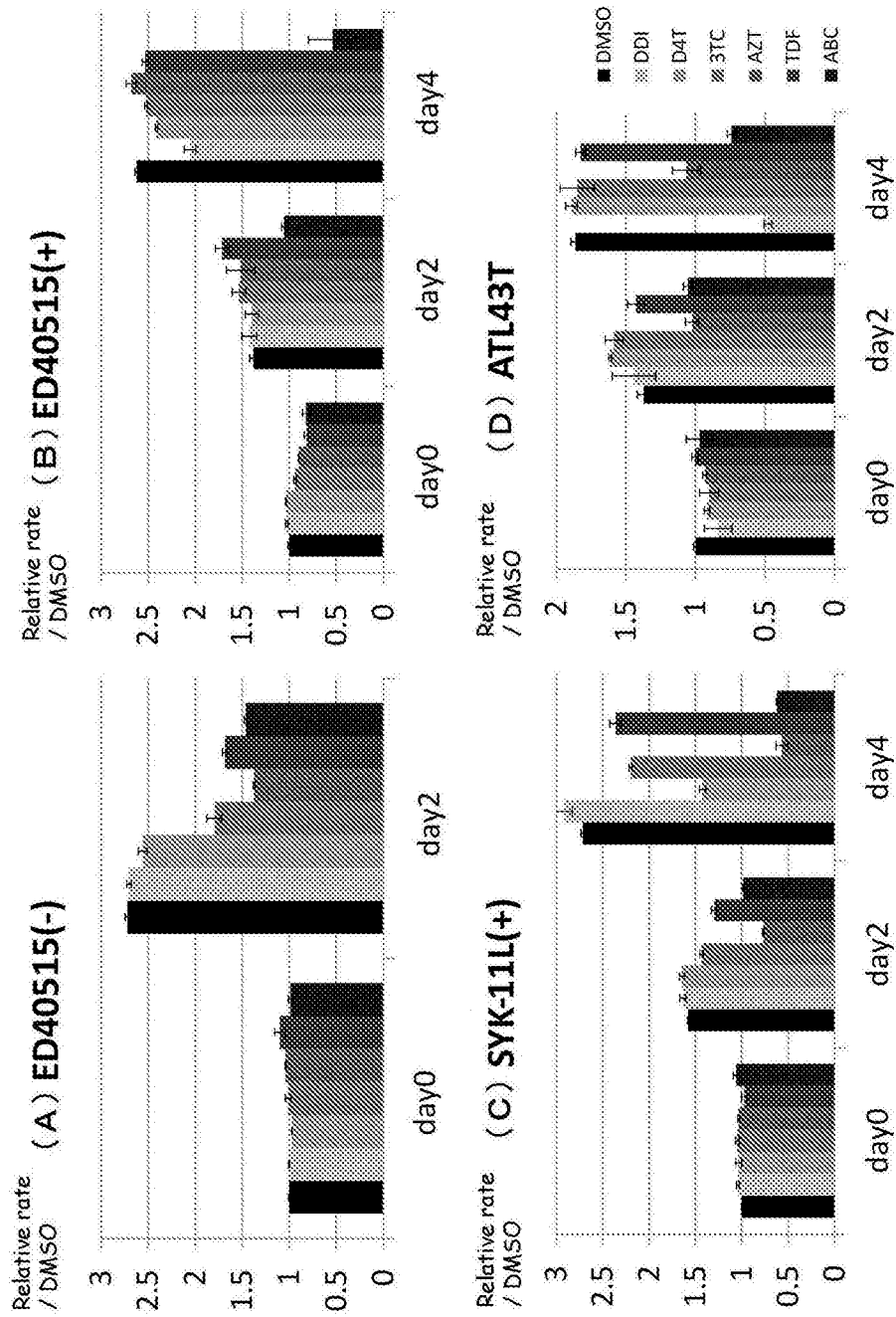
FIG. 3 shows the effects of six types of nucleoside analogue reverse transcriptase inhibitors on cellular proliferation of HTLV-1-infected cell lines (non-virus-producing ATL cell lines). The graphs (A), (B), (C), and (D) show the results of ED40515 (−), ED40515 (+), SYK-11L (+), and ATL43T, respectively.

The results are shown in FIG. 3, graphs (A) to (D). The graphs (A), (B), (C), and (D) show the results of ED40515 (−), ED40515 (+), SYK-11L (+), and ATL43T, respectively. As is apparent from FIG. 3, graphs (A) to (D), abacavir (ABC in the graphs) exhibited strong suppressive effect on cellular proliferation of all the cell lines.

Reference Example 1

Effect on Cellular Proliferation of Non-HTLV-1-Infected Cell Line

This example used non-HTLV-1-infected cell lines: Jurkat (cell line derived from human T-cell leukemia, ATCC No: TIB-152), Kit225 (cell line derived from chronic T-cell leukemia, established in the laboratory of the inventors, Blood. 1987 October; 70 (4): 1069-72.), H9 (cell line derived from cutaneous T-cell lymphoma, ATCC No: HTB-176) and SUDHL6 (cell line derived from diffuse B cell lymphoma).

The six types of nucleoside analogue reverse transcriptase inhibitors as used in Example 1 were used and cellular proliferation was examined in the same manner as in Example 1.

Figure 4:
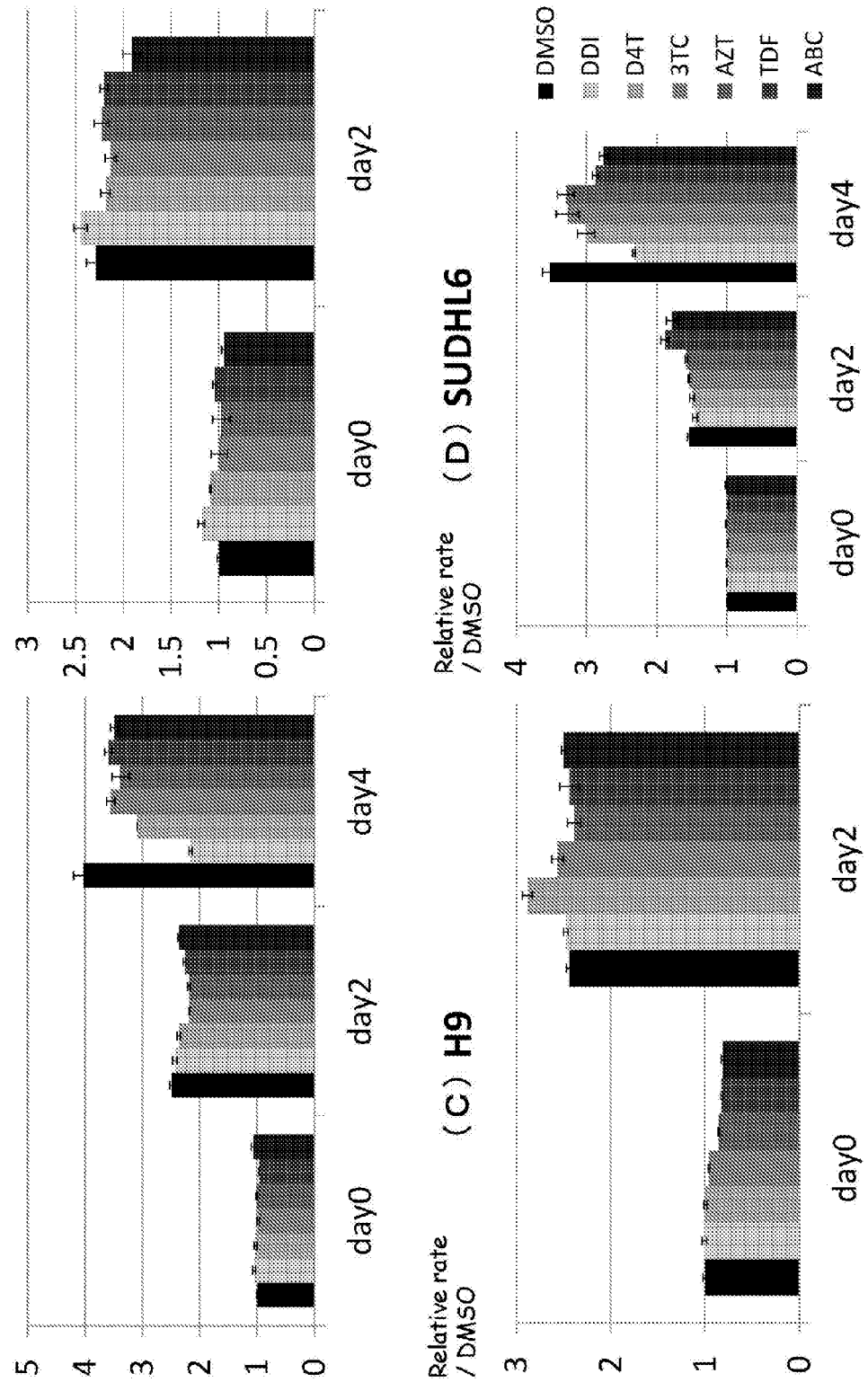
FIG. 4 shows the effects of six types of nucleoside analogue reverse transcriptase inhibitors on proliferation of non-HTLV-1-infected cell lines. The graphs (A), (B), (C), and (D) show the results of Jurkat, Kit225, H9, and SUDHL6, respectively.

The results are shown in FIG. 4, graphs (A) to (D). The graphs (A), (B), (C), and (D) show the results of Jurkat, Kit225, H9, and SUDHL6, respectively. As is apparent from FIG. 4, graphs (A) to (D), abacavir (ABC in the graphs) did not exhibit a suppressive effect on cellular proliferation of the cell lines.

Example 3

Suppression of Cellular Proliferation of HTLV-1-Producing Cell Line by Abacavir

Abacavir was added to MT2 and HUT102 used in Example 1 at a concentration of 0 μM (DMSO was added instead of abacavir), 10 μM, 25 μM, 50 μM, 75 μM or 100 μM. The cells were seeded on a 96-well plate at a concentration of $1 \times 10^4$ cells/100 μL/well and cultured for 4 hours or 48 hours. After the culture of a predetermined time, MTS assay was performed using a reagent for cellular proliferation test, Aqueous One Solution Cell Proliferation (trade name, manufactured by Promega), in the same manner as in Example 1. The cellular proliferation was represented by a ratio relative to that of the control (solvent control) on Day 0 that was regarded as 1.

Figure 5:
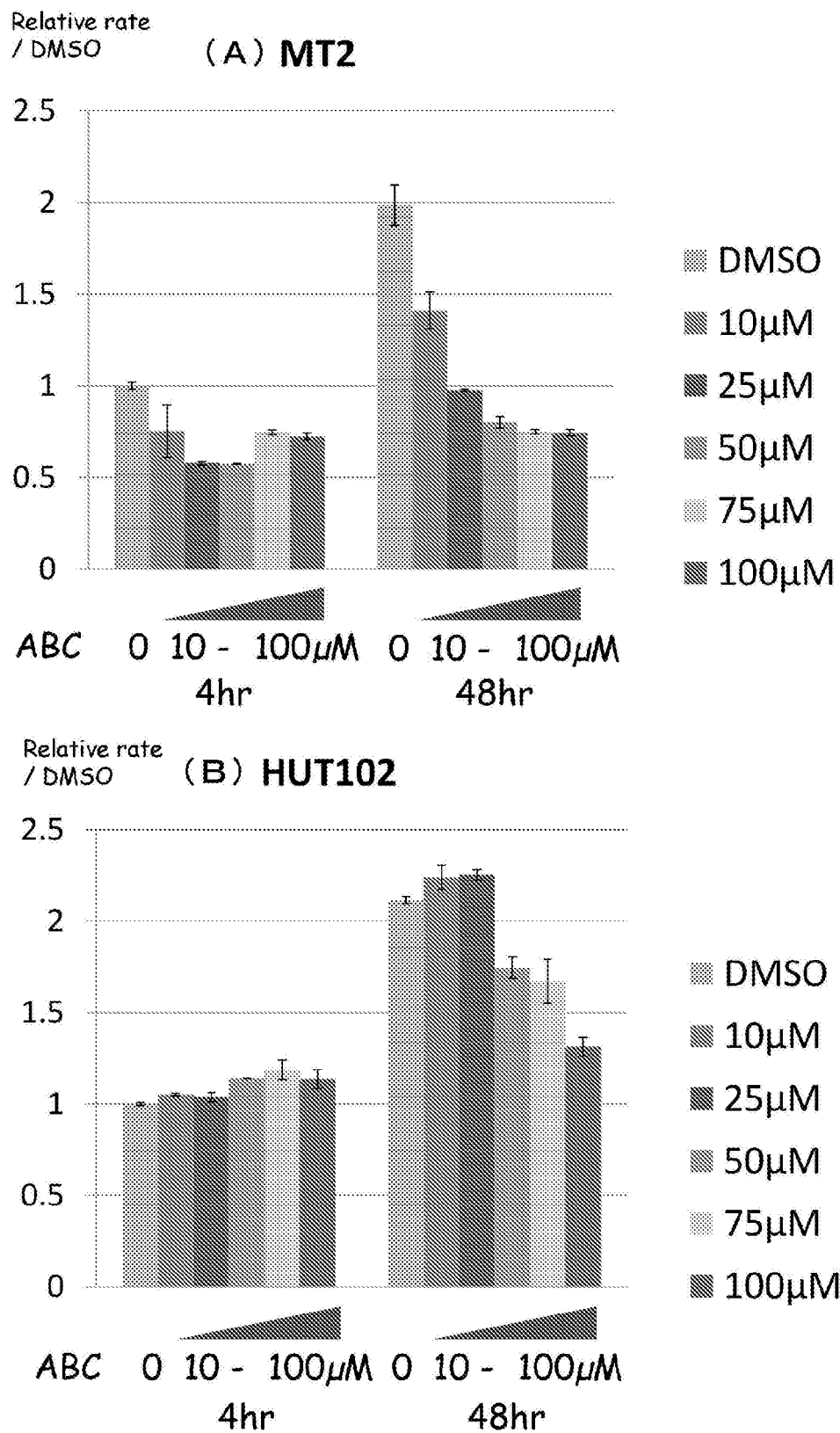
FIG. 5 shows the dose-dependent suppressive effect of abacavir on cellular proliferation of HTLV-1-producing cell lines. The graph (A) shows the results of MT2 and the graph (B) shows the results of HUT102.

The results are shown in FIG. 5, graphs (A) and (B). The graph (A) shows the results of MT2 and the graph (B) shows the results of HUT102. As is apparent from FIG. 5, graphs (A) and (B), abacavir suppressed cellular proliferation of both cell lines in a dose-dependent manner.

Example 4

Suppressive Effect of Abacavir on Cellular Proliferation of HTLV-1-Infected Cell Line (Non-Virus-Producing ATL Cell Line)

Abacavir was added to ED40515 (−), ED40515 (+), SYK-11L (+), and ATL43T used in Example 2 at a concentration of 0 μM (DMSO was added instead of abacavir), 10 μM, 25 μM, 50 μM, 75 μM or 100 μM. The cells were seeded on a 96-well plate at a concentration of $1 \times 10^4$ cells/100 μL/well and cultured for 4 hours (Day 0), 48 hours (Day 2) or 96 hours (Day 4). After the culture of a predetermined time, MTS assay was performed using a reagent for cellular proliferation, Aqueous One Solution Cell Proliferation (trade name, manufactured by Promega), in the same manner as in Example 1. The cellular proliferation was represented by a ratio relative to that of the control (solvent control) on Day 0 that was regarded as 1.

Figure 6:
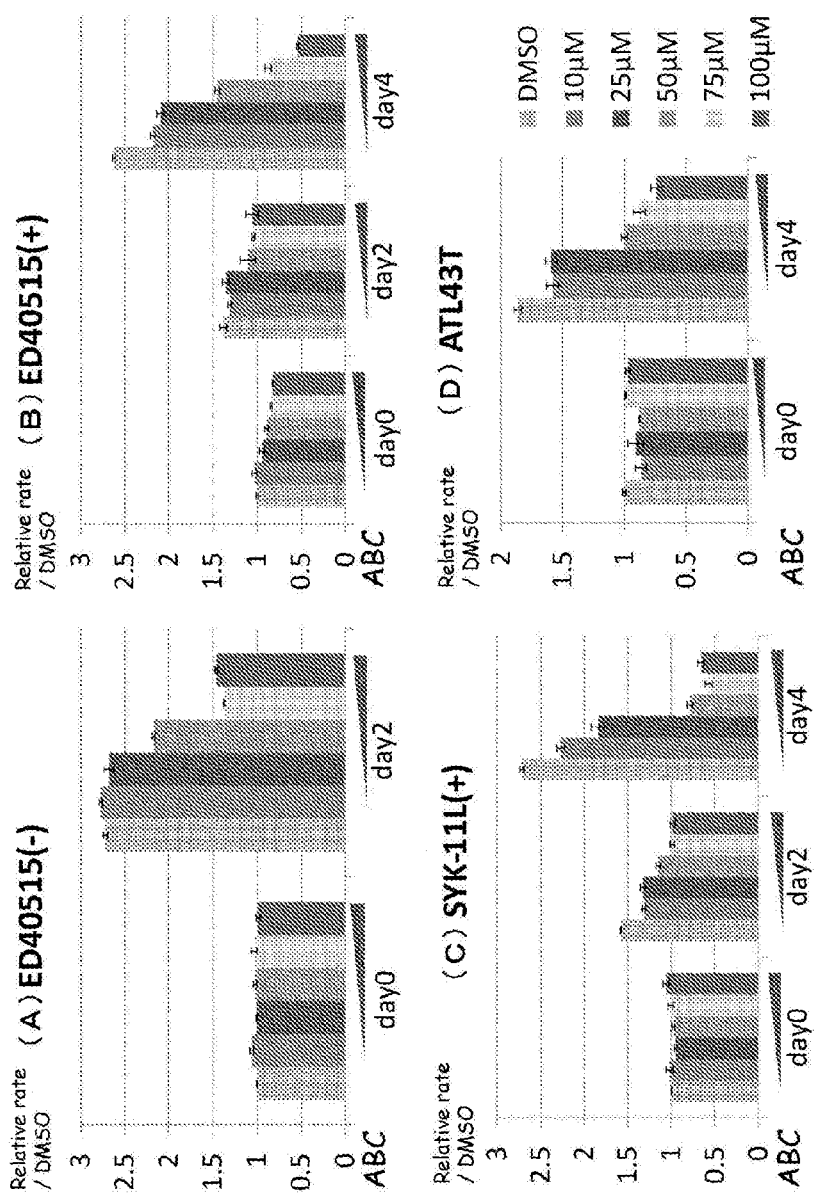
FIG. 6 shows the dose-dependent suppressive effect of abacavir on cellular proliferation of HTLV-1-infected cell lines (non-virus-producing ATL cell lines). The graphs (A), (B), (C), and (D) show the results of ED40515 (−), ED40515 (+), SYK-11L (+) and ATL43T, respectively.

The results are shown in FIG. 6, graphs (A) to (D). The graphs (A), (B), (C), and (D) show the results of ED40515 (−), ED40515 (+), SYK-11L (+), and ATL43T, respectively. As is apparent from FIG. 6, graphs (A) to (D), abacavir suppressed cellular proliferation of all the cell lines in a dose-dependent manner.

The results of Examples 1 to 4 and Reference Example 1 demonstrate that abacavir not only suppresses viral production in HTLV-1-infected cell lines but also strongly suppresses cellular proliferation of HTLV-1-infected cell lines including ATL cell lines. The effect of abacavir was specific to HTLV-1-infected T cell lines and not observed in other T-cell leukemia and B cell lymphoma cell lines.

Example 5

Effect of Abacavir on Chromosome of ATL Cell Line

Abacavir was added to an ATL cell line, ED40515 (−), at a concentration of 0 µM (DMSO was added instead of abacavir), 10 µM, 25 µM, 50 µM, 75 µM or 100 µM. After the 48 hours culture, the cells were fixed by Carnoy and stained with Giemsa to prepare chromosome specimens in accordance with conventional methods. Similarly, zidovudine was added to ED40515 (−) at a concentration of 10 µM or 100 µM, and abacavir was added to a non-ATL cell line, Jurkat, at a concentration of 100 µM, and chromosome specimens were prepared. Chromosome images (100 or more images per group) were observed by an optical microscope. The cells were determined as being positive for double-strand break (DSB) when at least one chromosome break was found.

Figure 7:
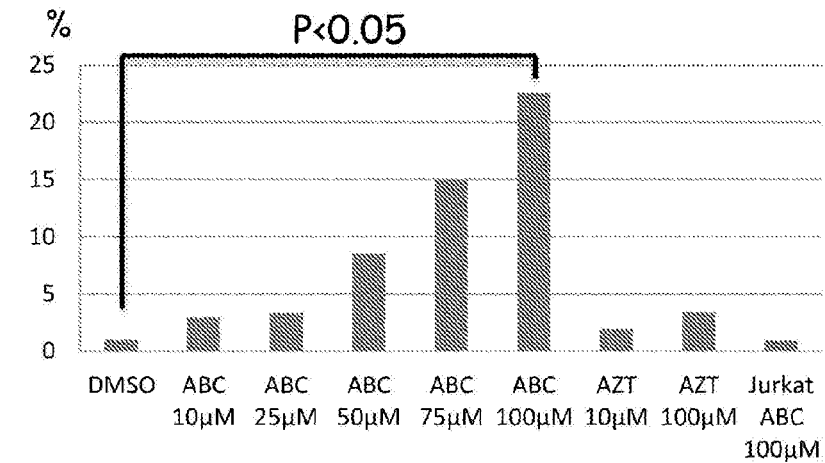
FIG. 7 shows the effect of abacavir on the chromosome of an ATL cell line.

The ratio of double-strand break-positive cells per group is shown in FIG. 7. As is apparent from FIG. 7, abacavir (ABC in the graph) increased the ratio of double-strand break-positive cells in a dose-dependent manner. In contrast, zidovudine (AZT in the graph) did not induce double-strand break in the chromosome of the ATL cell line. Further, abacavir did not induce double-strand break in the non-ATL cell line Jurkat.

Example 6

Induction of DNA Repair Protein by Abacavir Specifically in ATL Cell Line

To an ATL cell line, ED40515 (−), or a non-ATL cell line, Jurkat, DMSO (solvent control) or abacavir was added at a concentration of 100 µM. The cells were cultured for 48 hours. The cells were fixed on slides, immuno-stained for Rad51, γH2AX and PARP, and observed by a fluorescent microscope. At least 70 cells per group were observed and the ratio of cells positive for each protein was calculated. Rad51, which is a homologue of a RecA protein of *Escherichia coli*, is involved in repair of double-strand DNA break. γH2AX, which is a phosphorylated histone protein, is involved in repair of double-strand DNA break. PARP, which is a poly(ADP-ribose) synthetase, is involved in repair of single-strand DNA break.

Figure 8:
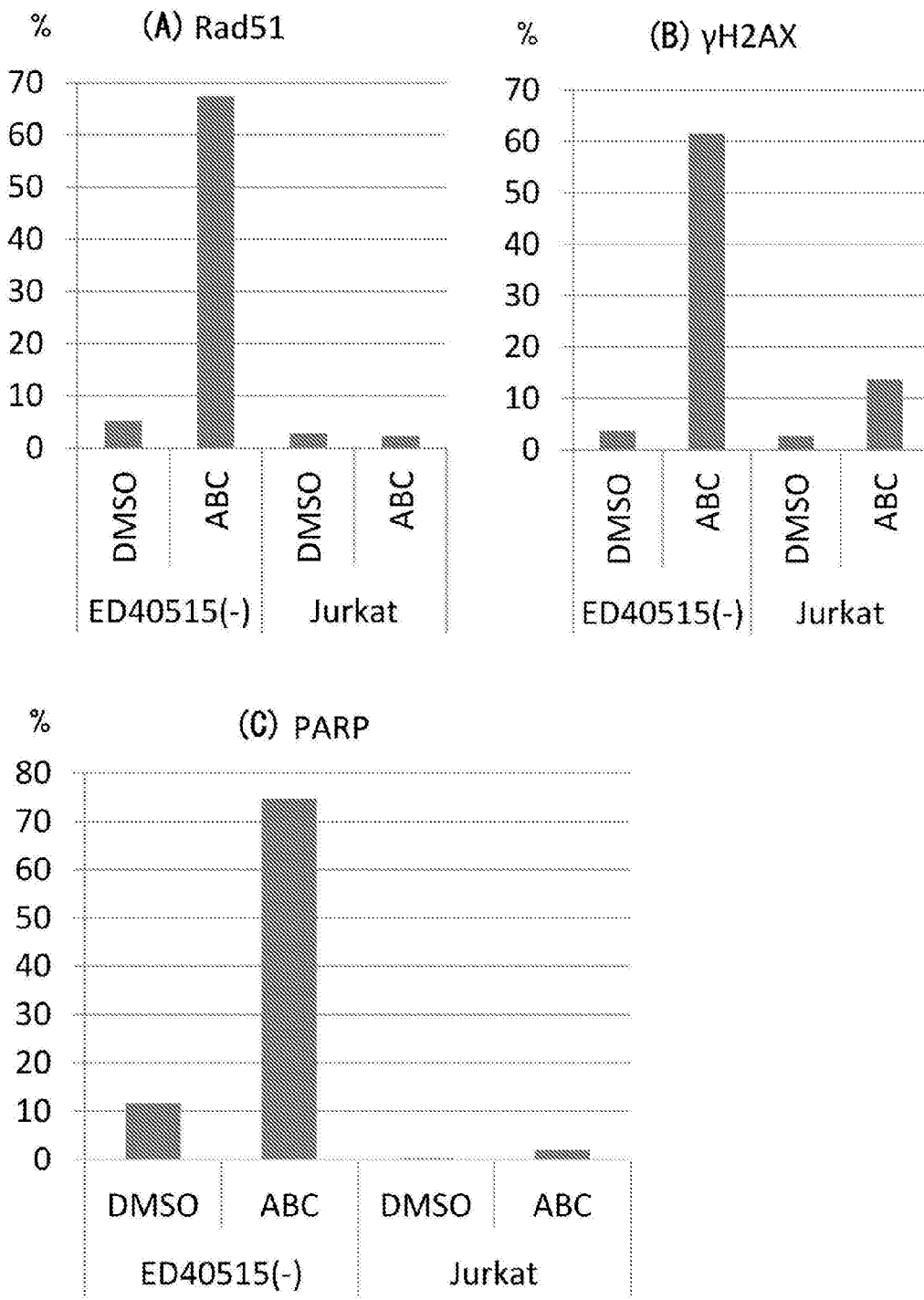
FIG. 8 shows the activity of abacavir specific to an ATL cell line to induce DNA repair proteins. The graphs (A), (B), and (C) show the ratios of Rad51 positive cells, γH2AX positive cells, and PARP positive cells, respectively.

The results are shown in FIG. 8, graphs (A) to (C). The graphs (A), (B), and (C) show the ratios of Rad51[+] cells, γH2AX[+] cells, and PARP[+] cells, respectively. FIG. 8, graphs (A) to (C) clearly shows that abacavir (ABC in the graphs) induces Rad51, γH2AX, and PARP specifically in an ATL cell line. The results demonstrate that abacavir induces DNA double-strand break in the ATL cell-specific manner.

Example 7

Effect of PARP Inhibitor on Suppression of ATL Cellar Proliferation by Abacavir

To an ATL cell line, ED40515 (−), or a non-ATL cell line, Jurkat, abacavir was added at a concentration of 0 µM (DMSO, was added instead of abacavir), 10 µM, 50 µM or 100 µM, and further a PARP inhibitor, olaparib, was added at a concentration of 0 µM (DMSO was added instead of olaparib), 1 µM, 10 µM, 100 µM or 1000 µM. The cells were cultured for 48 hours. MTS assay was performed using a reagent for cellular proliferation test, Aqueous One Solution Cell Proliferation (trade name, manufactured by Promega), in the same manner as in Example 1. The cellular proliferation was represented by a ratio relative to that of the control (solvent control) on Day 0 that was regarded as 1.

Figure 9:
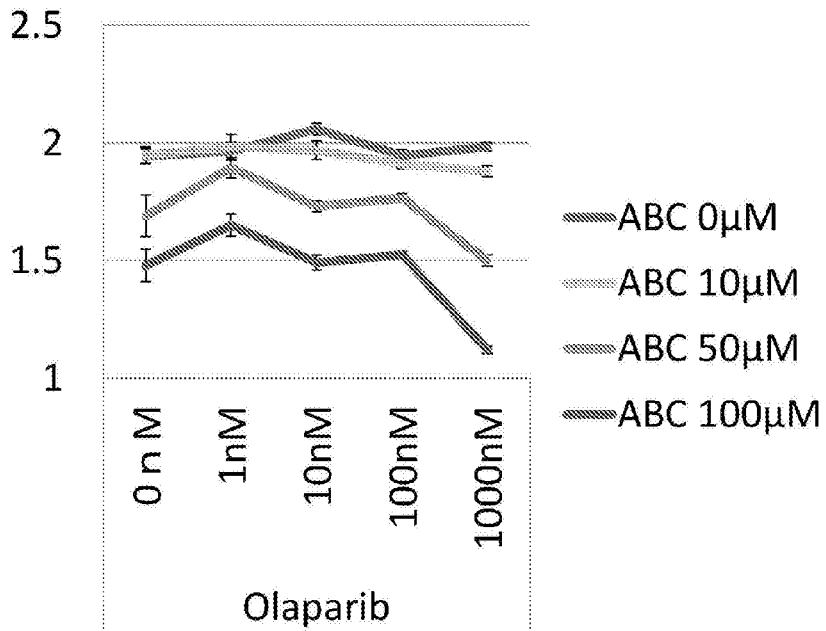
FIG. 9 shows the effect of a PARP (poly(ADP-ribose) polymerase) inhibitor on the suppressive effect of abacavir on ATL cellular proliferation.
Figure 9:
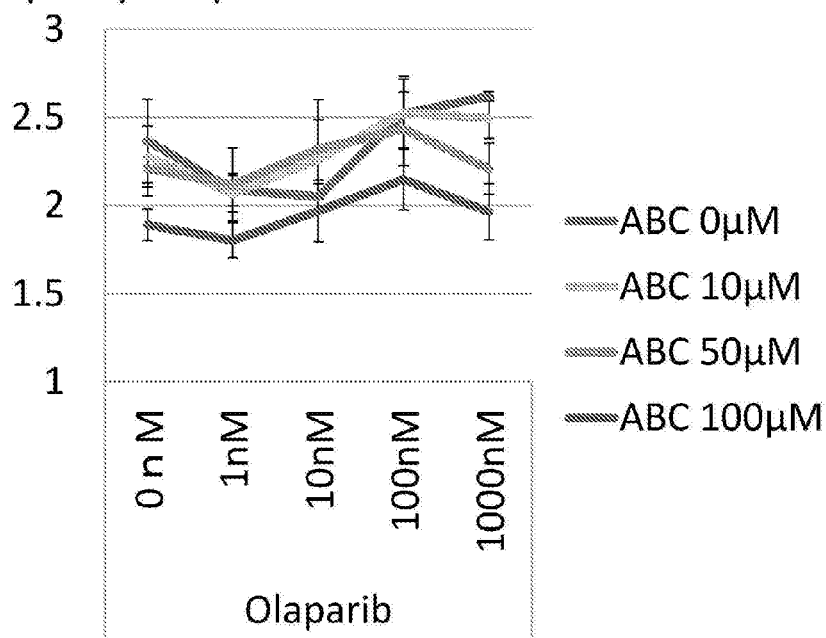

The results are shown in FIG. 9, graphs (A) and (B). The graph (A) shows the results of ED40515 (−) and the graph (B) shows the results of Jurkat. As is apparent from FIG. 9, graph (A), olaparib enhanced the suppressive effect of abacavir (ABC in the graph) on ED40515 (−) cellular proliferation in a dose-dependent manner. In contrast, as is apparent from FIG. 9, graph (B), abacavir (ABC in the graph) did not suppress cellular proliferation of Jurkat, and olaparib did not affect cellular proliferation of Jurkat.

Example 8

Effect of Abacavir on Cell Cycle of ATL Cell Line

To an ATL cell line, ED40515 (−), or a non-ATL cell line, Jurkat, DMSO (solvent control), adriamycin (ADR, positive control) or abacavir (10 µM or 100 µM) was added. The cells were cultured for 24 hours, stained with propidium iodide (PI) and subjected to cell-cycle analysis by flow cytometry to obtain the ratio of cells in the GOG1/S/G2 phase.

Figure 10:
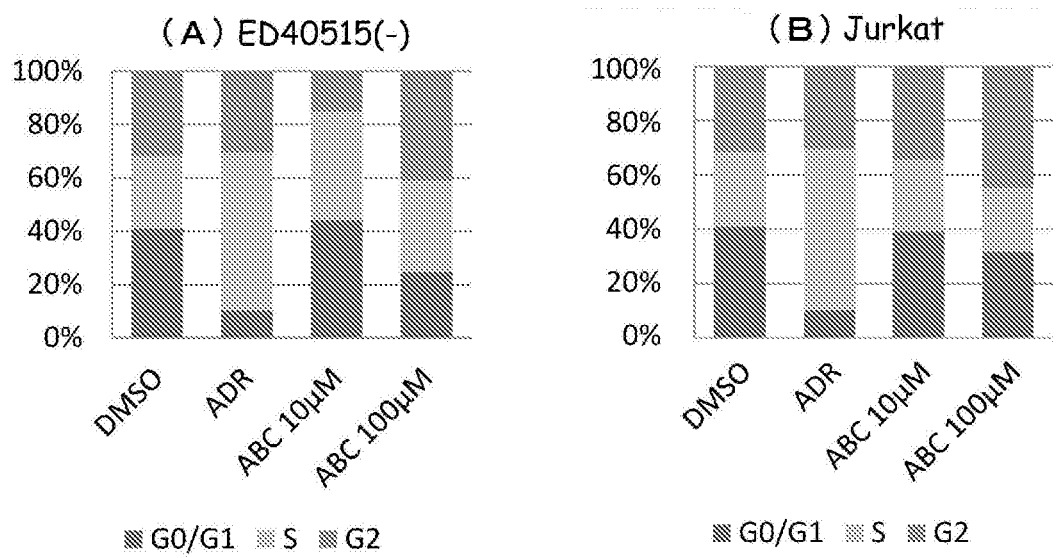
FIG. 10 shows the effect of abacavir on the cell cycle of an ATL cell line.

The results are shown in FIG. 10, graphs (A) and (B). The graph (A) shows the results of ED40515 (−) and the graph (B) the results of Jurkat. As is apparent from FIG. 10, graph (A), abacavir (ABC in the graph) induced the S/G2 arrest in ED40515 (−). In contrast, as is apparent from FIG. 10, graph (B), abacavir (ABC in the graph) did not affect the cell cycle of Jurkat.

Example 9

Apoptosis-Inducing Activity of Abacavir in ATL Cell Line

DMSO (solvent control), adriamycin (ADR, positive control), or abacavir (100 µM) was added to an ATL cell line, ED40515 (−). The cells were cultured for 24 hours or 48 hours. After the culture of a predetermined time, the cells were stained with annexin V, and annexin V positive cells were measured by flow cytometry. The annexin V positive cells were determined as apoptotic cells.

Figure 11:
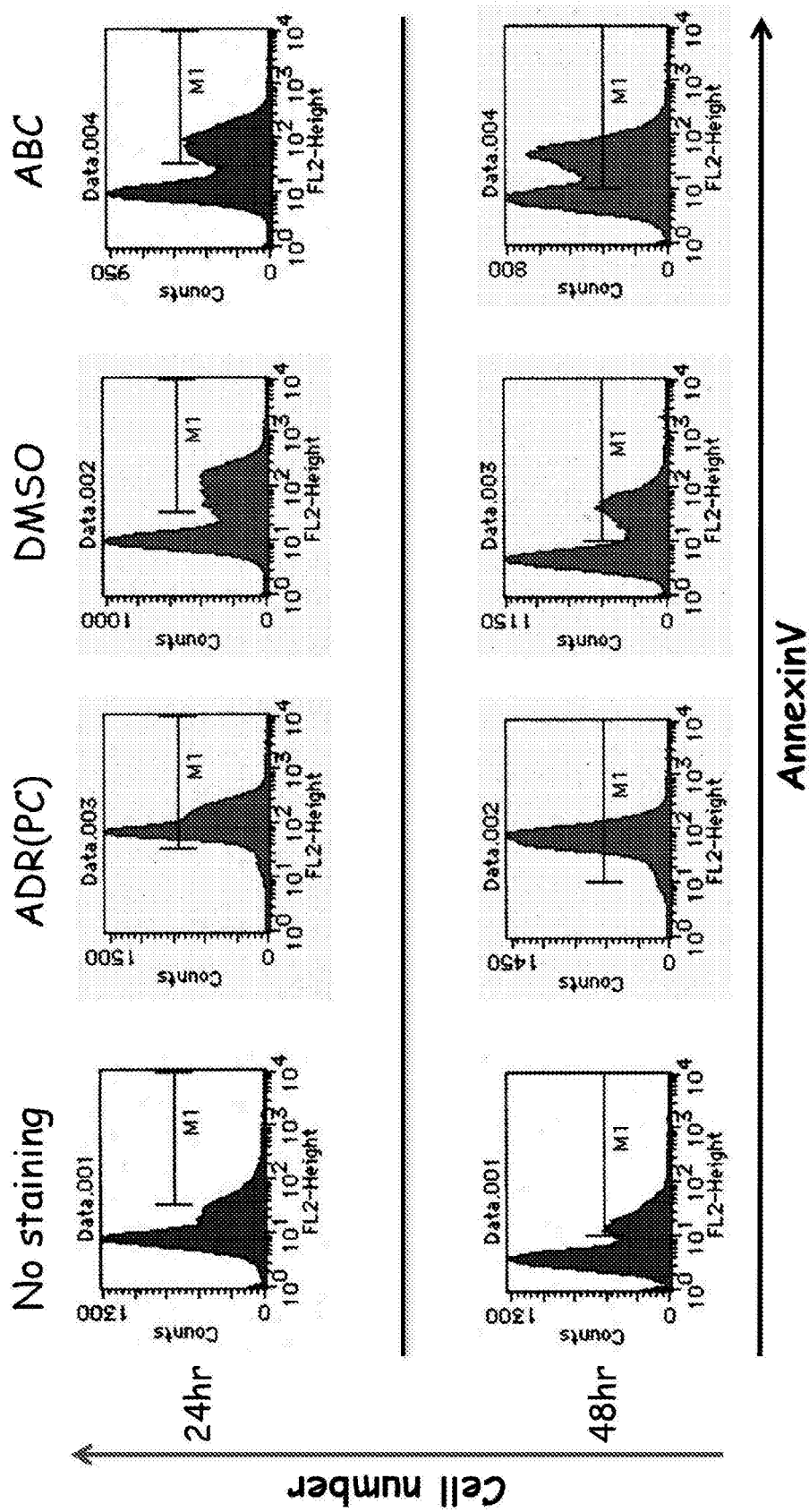
FIG. 11 shows the apoptosis-inducing activity of abacavir on an ATL cell line.

The results are shown in FIG. 11. As is apparent from FIG. 11, abacavir (ABC in the graph) induced apoptosis in ED40515 (−).

The results of Examples 5 to 9 demonstrate that abacavir induces chromosome break in ATL cell lines but does not affect non-ATL cell lines. This effect of abacavir was not observed with zidovudine, a nucleoside analogue reverse transcriptase inhibitor that has been reported to cause DNA damage. Thus, it was revealed that abacavir induces chromosome break in an ATL cell-specific manner and the effect is specific to abacavir. Further, it was demonstrated that abacavir arrests cell-cycle to cause apoptosis in ATL cells.

Example 10

Effect of Abacavir on Cellular Proliferation of DT40-Derived Mutant Lacking DNA Repair Enzyme This example used wild-type DT40, which is a chicken B cell-derived cell line, and DT40-derived mutants each lacking a DNA repair enzyme. Those cell lines are available from the laboratory of Radiation Genetics, Graduate School of Medicine and Faculty of Medicine Kyoto University (see, Literatures: (1) Mol Cell Biol. 2001 April; 21 (8): 2858-66. (2) PLoS Genet. 2011 July; 7 (7): e1002148. (3) Mol Cell Biol. 2008 October; 28 (19): 6113-22. (4) J Biol Chem. 2012 Apr. 13; 287 (16): 12848-57.).

Abacavir was added to the medium of each cell line at a final concentration of 25 µM. The cells were seeded on a 96-well plate at a concentration of $1 \times 10^4$ cells/100 µL/well and cultured for 48 hours. After the culture, cellular proliferation was determined by CellTiter-Glo Luminescent Cell Viability Assay (trade name, manufactured by Promega) in accordance with the ATP method.

Figure 12:
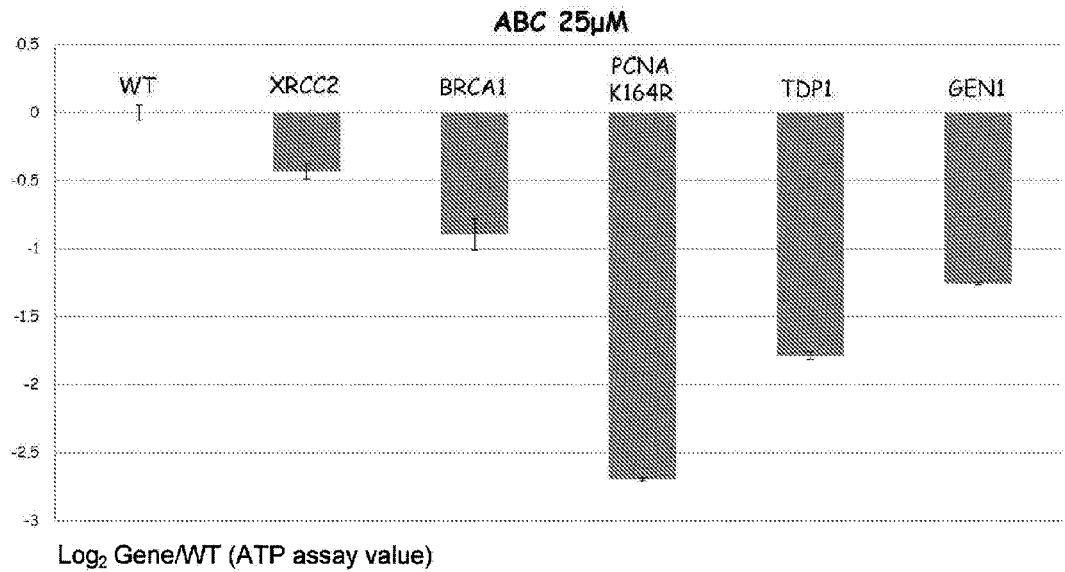
FIG. 12 shows the effect of abacavir on cellular proliferation of DT40-derived mutants each lacking a DNA repair enzyme.

The results are shown in FIG. 12. In FIG. 12, the vertical axis ($Log_2$ Gene/WT) shows a numerical value obtained by dividing the ATP assay value of a DT40-derived mutant lacking a DNA repair enzyme by that of the wild-type DT40 and taking log 2 of the resulting quotient. Specifically, the value on the vertical axis is −1 when the proliferation rate compared to the wild-type is 50%, and −2 when the proliferation rate compared to the wild-type is 25%. As is apparent from FIG. 12, abacavir showed a suppressive effect on cellular proliferation of the DT40 mutant, each of which lacks a DNA repair enzyme, XRCC2, PCNA, BRCA1, TDP1 or GEN1. Abacavir also showed a similar suppressive effect on different DT40-derived mutants each lacking a different DNA repair enzyme (data not shown). Those results demonstrate that abacavir is useful not only for HTLV-1-infected cells but also for the prevention or the treatment of a cancer whose DNA repair system is impaired.

Example 11

Expression of TDP1 in HTLV-1-Infected Cell Line

HTLV-1-infected cell lines, ED40515 (−), ED40515 (+), MT2, HUT102, SY, SYK-11L (+), and ATL43T were used. A non-HTLV-1-infected cell line, Jurkat, was used as a control. These cell lines except for SY cell line were the same as those used in Examples 1 and 2 or Reference Example 1. The SY cell line is an HTLV-1-infected cell line prepared in the laboratory of the inventors. In accordance with conventional methods, the cell lines were cultured and used to prepare cell lysates, and TDP1 in the cell lysates was detected by Western blot. Specifically, each of the cell lines was separately lysed in a lysis buffer (MPER, 1 mM PMSF, phosphatase inhibitor cocktail, protease inhibitor cocktail) and the resulting lysate was developed by SDS-PAGE, followed by transfer to a membrane and detection by an anti-rabbit TDP1 antibody (ab4166: Abcam).

Figure 13:
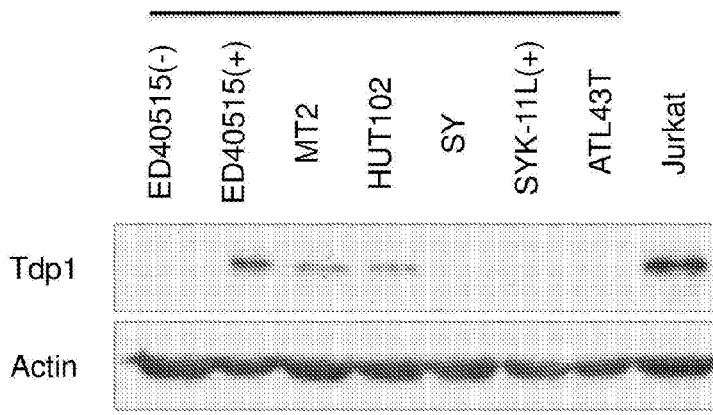
FIG. 13 shows the expression level of TDP1 protein in HTLV-1-infected cell lines detected by Western blot.

The results are shown in FIG. 13. As is apparent from FIG. 13, the HTLV-1-infected cell lines showed a reduced level of TDP1 protein. Those results demonstrate that DNA repair system involving TDP1 is impaired in HTLV-1-infected cell lines.

Example 12

Expression of TDP1 in Cells Derived from ATL Patients

Peripheral mononuclear cells collected from ten ATL patients, and CD4+ T cells collected from five healthy persons, were used in this test. Western blot was performed in the same manner as in Example 11. Further, total RNA was extracted from each of the cells and cDNA was synthesized and subjected to quantitative PCR to quantify the amount of TDP1 mRNA. Specifically, RNA was extracted using High Pure RNA Isolation Kit (Roche), and cDNA was synthesized using PrimeScriptII $1^{st}$ strand cDNA Synthesis Kit. The amount of TDP1 mRNA was quantified using the following primers.

```
                                          (SEQ ID NO: 1)
TDP1_F: 5'-AGGCAGCCTTGGAcaGATT-3'

(SEQ ID NO: 2)
TDP1_R: 5'-GGTCAGCTGAGACTTCTGGC-3'
```

Figure 14:
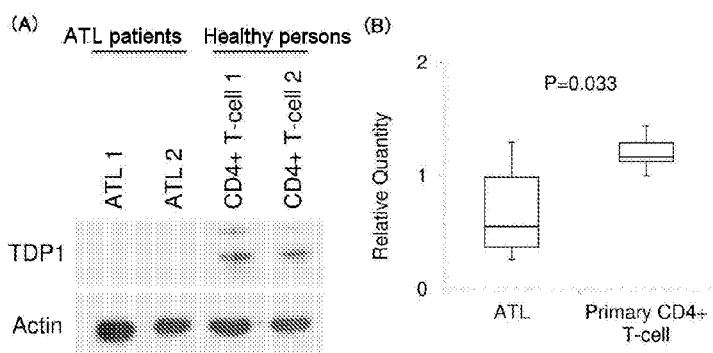
FIG. 14 shows the comparison of expression level of TDP1 between peripheral mononuclear cells of ATL patients and CD4⁺ T cell of healthy persons. The graph (A) shows the results of Western blot and the graph (B) shows the results of quantitative PCR.

The results are shown in FIG. 14, graphs (A) and (B). FIG. 14, graph (A) shows the results of Western blot for two ATL patients and two healthy persons and FIG. 14, graph (B) shows the results of quantitative PCR for ten ATL patients and five healthy persons. As is apparent from FIG. 14, graph (A), TDP1 protein was not detected in peripheral mononuclear cells of the ATL patients. As is also apparent from FIG. 14, graph (B), the expression level of TDP1 mRNA in the ATL patients was significantly lower than that of the healthy persons. In FIG. 14, graph (B), the expression level of TDP1 mRNA is represented by a ratio relative to that of one of the healthy persons that is regarded as 1.

Example 13

Acquisition of Sensitivity to Abacavir by TDP1 Knockdown (1) Preparation of TDP1-Knocked-Down Cells siRNA for TDP1 was introduced into a non-HTLV-1-infected cell line, Jurkat, by electroporation to prepare a TDP1-knocked-down cell. Specifically, siRNA was introduced by the AMAXA system using siTDP1 SMART POOL (Dharmacon) purchased and Human Cell Nucleofector Kit (LONZA). After 24 hours from the siRNA introduction, quantitative PCR was performed in the same manner as in Example 12 to measure the amount of TDP1 mRNA. Also, after 72 hours from the siRNA introduction, a cell lysate was prepared and Western blot was performed in the same manner as in Example 11 to detect expression of TDP1 protein. In both experiments, the control sample was prepared from Jurkat cells into which a control siRNA was introduced. The control siRNA was Stealth RNAi negative control (Invitrogen).

Figure 15:
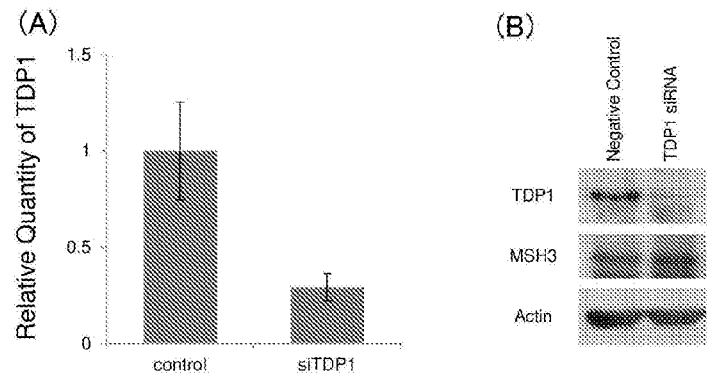
FIG. 15 shows the expression level of TDP1 in TDP1-knocked-down cells prepared by introducing TDP1 siRNA into cells of a non-HTLV-1-infected cell line, Jurkat. The graph (A) shows the results of quantitative PCR and the graph (B) shows the results of Western blot.

The results are shown in FIG. 15, graphs (A) and (B). The graph (A) shows the results of quantitative PCR and the graph (B) shows the results of Western blot. As is apparent from FIG. 15, graph (A), the amount of TDP1 mRNA in the TDP1-knocked-down cells was significantly lower than that of the control. As is apparent from FIG. 15, graph (B), the expression level of TDP1 protein in the TDP1-knocked-down cells was significantly lower than that of the control. Those results confirmed successful preparation of desired TDP1-knocked-down cells.

(2) Effect of Abacavir on Cellular Proliferation of TDP1-Knocked-Down Cells

This experiment used TDP1-knocked-down cells and control cells, which were prepared by introducing a TDP1 siRNA or a control siRNA into Jurkat, respectively. After the introduction of siRNA, abacavir was added to the medium of each of the cells at a concentration of 0 μM (DMSO was added instead of abacavir) or 300 μM. The cells were cultured for 48 hours. MTS assay was performed using a reagent for cellular proliferation test, Aqueous One Solution Cell Proliferation (trade name, manufactured by Promega), in the same manner as in Example 1.

Figure 16:
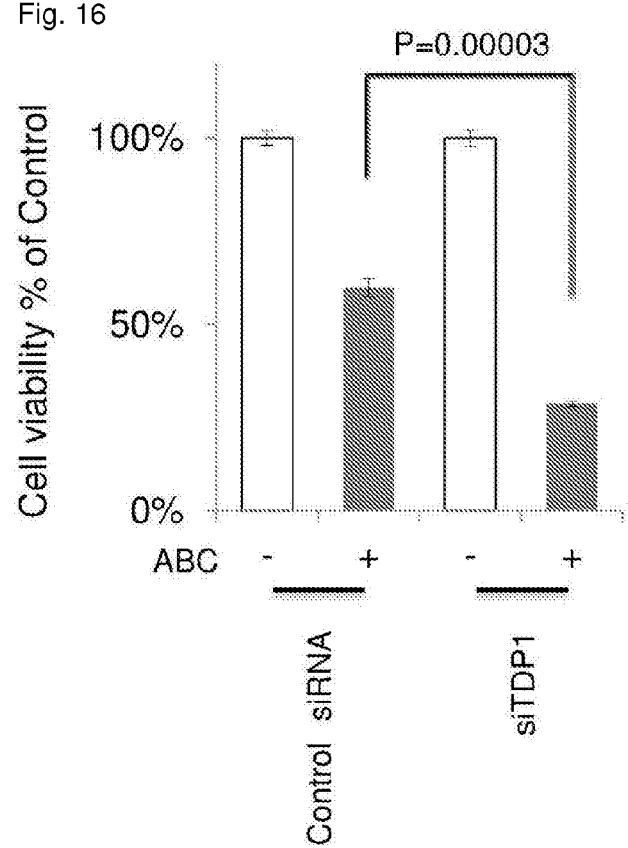
FIG. 16 shows the suppressive effect of abacavir on cellular proliferation of TDP1-knocked-down cells.

The results are shown in FIG. 16. For both TDP1 siRNA-introduced cells and control siRNA-introduced cells, cellular proliferation of abacavir (ABC in the graph)-treated cells is represented by a relative value to that of abacavir-non-treated cells that is regarded as 100%. As is apparent from FIG. 16, cellular proliferation of TDP1-knocked-down cells, into which TDP1 siRNA was introduced, was significantly lower than that of the control siRNA-introduced cells. Those results demonstrate that abacavir is effective to cancer cells expressing a reduced level of TDP1.

Example 14

Loss of Sensitivity to Abacavir by Introduction of TDP1 to MT2 Cells (1) Preparation of TDP1-Overexpressing MT2 Cells To the HTLV-1-infected cell line, MT2, which was confirmed to express a reduced level of TDP1 protein in Example 11, a lentivirus vector for expressing human TDP1 was introduced to prepare MT2 cell overexpressing human TDP1 protein. An empty vector (mock) was introduced to prepare the control. The lentivirus vector for human TDP1 expression was provided by the NIH. In accordance with conventional methods, the cells were cultured, and expression of TDP1 protein was detected by Western blot in the same manner as in Example 11.

Figure 17:
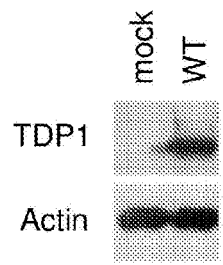
FIG. 17 shows the expression level of TDP1 protein detected by Western blot in TDP1-overexpressing MT2 cells prepared by introducing a human TDP1-expressing lentivirus vector to an HTLV-1-infected cell line, MT2.

The results are shown in FIG. 17. TDP1 protein was not detected in the control cells (mock in the figure) but detected in the cells into which the TDP1-expressing lentivirus vector was introduced (WT in the figure). Those results confirmed preparation of desired MT2 cells overexpressing TDP1.

(2) Effect of Abacavir on Cellular Proliferation of TDP1-Overexpressing MT2 Cells Abacavir was added to each of the TDP1-overexpressing MT2 cells and the control cells (mock) at a concentration of 0 μM (DMSO was added instead of abacavir), 10 μM, 25 μM, 50 μM, 75 μM or 100 μM. The cells were cultured for 48 hours. MTS assay was performed using a reagent for cellular proliferation test, Aqueous One Solution Cell Proliferation (trade name, manufactured by Promega), in the same manner as in Example 1.

Figure 18:
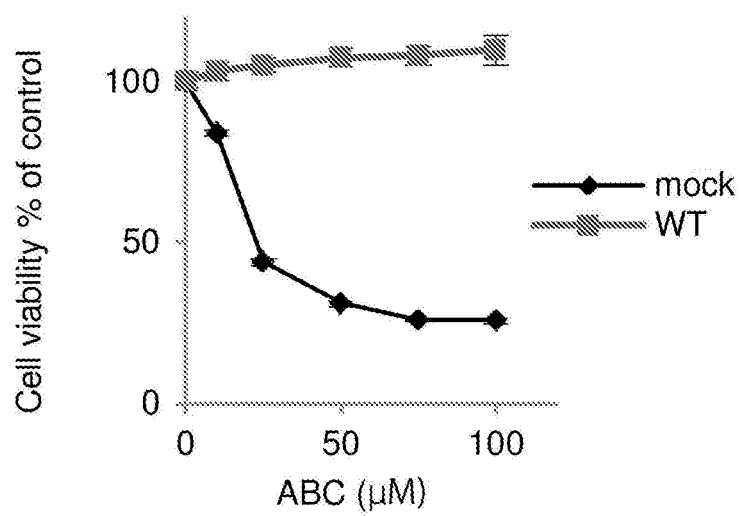
FIG. 18 shows the suppressive effect of abacavir on cellular proliferation of TDP1-overexpressing MT2 cells.

The results are shown in FIG. 18. Cellular proliferation of each of the treatment groups was represented by a relative value to that of the control cells (mock in the graph) not treated with abacavir (ABC in the graph) that was regarded as 100%. As is apparent from FIG. 18, cellular proliferation of TDP1-overexpresssing MT2 cells (WT in the graph) was not suppressed even with an increased concentration of abacavir. Specifically, it was demonstrated that MT2 cells being sensitive to abacavir in nature lose the sensitivity when TDP1 is overexpressed.

Example 15

Effect of Abacavir on Cellular Proliferation of Lung Cancer Cell Line

Lung cancer cell lines lacking TDP1 expression, HOP_62 and NCI_H522, were used. NCI_H1299, a lung cancer cell line expressing TDP1, was used as a control. HOP_62 and NCI_H522 were provided by Dr. Pommier (DNA Repair. 2014 January; 13: 1-9).

Abacavir was added to each of the cell lines at a concentration of 0 μM (DMSO was added instead of abacavir), 100 μM, 200 μM or 300 μM. The cells were seeded on a 96-well plate at a concentration of $3 \times 10^3$ cells/100 μL/well and cultured for 4 hours or 72 hours. After the culture of a predetermined time, MTS assay was performed using a reagent for cellular proliferation, test, Aqueous One Solution Cell Proliferation (trade name, manufactured by Promega), in the same manner as in Example 1. The cellular proliferation was represented by a ratio relative to that of the control (solvent control) on Day 0 that was regarded as 100%.

Figure 19:
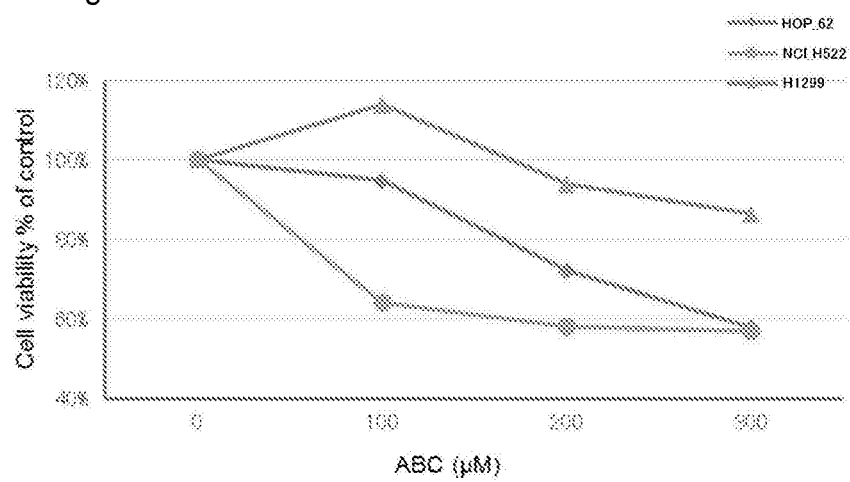
FIG. 19 shows the suppressive effect of abacavir on cellular proliferation of a lung cancer cell line lacking TDP1 expression.

The results are shown in FIG. 19. As is apparent from FIG. 19, abacavir suppressed cellular proliferation of HOP_62 and NCI_H522 lacking TDP1 expression in a concentration dependent manner. Those results demonstrate that abacavir is effective for lung cancer expressing a reduced level of TDP1.

Example 16

Effect of Combination of Abacavir and Topoisomerase Inhibitor

An HTLV-1-infected cell line, MT2 cell, was used. Abacavir was added at a concentration of 0 μM (DMSO was added instead of abacavir), 10 μM, or 25 μM, and to each of the samples, CPT-11 (generic name: irinotecan) was further added at a concentration of 0 pM, 200 pM, 300 pM, or 400 pM. The cells were cultured for 48 hours. Separately, abacavir was added to MT2 cells at the concentrations as described above, and VP16 (generic name: etoposide) was further added to each of the samples at a concentration of 0 nM, 100 nM, 250 nM, or 500 nM, followed by 48 hours culture. Separately, abacavir was added to MT2 cells at the concentrations as described above, and ADR (generic name: doxorubicin) was further added at a concentration of 0 nM, 10 nM, 25 nM, or 50 nM, followed by 48 hours culture. MTS assay was performed using a reagent for cellular proliferation test, Aqueous One Solution Cell Proliferation (trade name, manufactured by Promega), in the same manner as in Example 1.

The results are shown in FIG. 20, graphs (A) to (C). The graphs (A), (B), and (c) show the results of combinations of abacavir (ABC in the graph) and CPT-11, abacavir and VP16, and abacavir and ADR, respectively. In the graphs, the vertical axis indicates the proliferation rate calculated from the cell number when the cell number at the administration of the agents was regarded as 1. As is apparent from FIG. 20, graphs (A) to (C), all the topoisomerase inhibitors significantly suppressed cellular proliferation of MT2 in combination with abacavir.

The present invention is not limited to the embodiments and Examples described above and can be modified in various ways within the scope of the claims. Any embodiment obtained by appropriately combining technical features disclosed in different embodiments also falls within the scope of the present invention. Further, all the academic documents and patent literatures described in the specification are incorporated herein by reference.

The invention claimed is:

1. A method for treating a cancer whose DNA repair system is impaired, comprising administering abacavir or a pharmaceutically acceptable salt thereof to a mammal in an amount of 5 to 60 mg per kg of body weight per day, wherein the cancer is adult T-cell leukemia (ATL) or lung cancer.

2. The method according to claim 1, wherein the cancer is a cancer expressing a reduced level of TDP1.

3. The method according to claim 1, wherein the cancer is lung cancer or a cancer caused by infection with human T-cell leukemia virus type 1.

4. The method according to claim 1, wherein the cancer is adult T-cell leukemia.

5. The method according to claim 1, further comprising administering an effective amount of a PARP inhibitor to the mammal.

6. The method according to claim 1, further comprising administering an effective amount of a topoisomerase inhibitor to the mammal.

7. The method according to claim 1, wherein DNA cleavage is induced.

8. The method according to claim 1, wherein cell cycle arrest and/or apoptosis is induced.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
aggcagcctt ggacagatt                                               19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ggtcagctga gacttctggc                                              20
```